United States Patent [19]

Eison et al.

[11] Patent Number: 4,859,666

[45] Date of Patent: Aug. 22, 1989

[54] THAZ DERIVATIVES FOR ENHANCEMENT OF CEREBRAL FUNCTION

[75] Inventors: Michael S. Eison, Avon, Conn.; Povl Krogsgaard-Larsen, Allerod, Denmark

[73] Assignee: Bristol-Myers Company, New York, N.Y.

[21] Appl. No.: 215,836

[22] Filed: Jul. 6, 1988

[51] Int. Cl.$^4$ ............... A61K 31/395; C07D 223/00
[52] U.S. Cl. ...................... 514/221; 540/578
[58] Field of Search .................. 540/578; 514/221

[56] References Cited

U.S. PATENT DOCUMENTS 4,668,687 5/1987 Yevich et al. .................. 514/252

OTHER PUBLICATIONS

Butler, et al., *J. Med. Chem.*, 27: 284-691 (1984).
Krogsgaard-Larsen, et al., *J. Neurochem.*, 39/5: 1319-1324 (1982).
Krogsgaard-Larsen, et al., *Acta Chem. Scand.*, B28: 533-538 (1974).
Braestrup, et al., *J. Neurochem.*, 47/3: 691-696 (1986).

*Primary Examiner*—Mary C. Lee
*Assistant Examiner*—J. Richter
*Attorney, Agent, or Firm*—Richard P. Ryan

[57] ABSTRACT

Tetrahydro-isoxazolo[4,5-d]azepine derivatives possess antiamnesic properties and are cognition enhancers.

15 Claims, No Drawings

THAZ DERIVATIVES FOR ENHANCEMENT OF CEREBRAL FUNCTION

BACKGROUND OF THE INVENTION

This invention pertains to heterocyclic carbon compounds having drug and bio-affecting properties and to their preparation and use. In particular, the invention is concerned with 5,6,7,8-tetrahydro-4-H-isoxazolo [4,5-d]- azepin-3-ol derivatives. The compounds of this invention are cerebral function enhancers useful in treatment of various dementias due to degenerative processes as well as enhancing memory and learning.

Clinical aspects of various degenerative dementias as well as the socioeconomic problems which result in affected populations are readily appreciated by those familiar with the art. Various drug treatments directed to these disorders are currently under study. Among such drugs are a class of compounds known as nootropic agents or, more commonly, cognition enhancers. Some representatives of this class of compounds are currently being evaluated clinically for treatment of patients diagnosed as having Alzheimer's disease, a serious and fairly common CNS disorder of the elderly. Chemically, these drugs are members of a class of N-substituted-2-pyrrolidinone derivatives of formula 1:

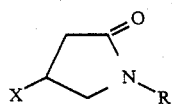

(a) X=H, R=—CH$_2$CONH$_2$ (piracetam);
(b) X=OH, R=—CH$_2$CONH$_2$ (oxiracetam);
(c) X=H, R=—CH$_2$CONHCH$_2$ CH$_2$N[CH(CH$_3$)$_2$]$_2$ (pramiracetam);
(d) X=H,

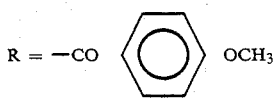

(aniracetam).

Butler, et al., *J. Med. Chem.*, 27, pp. 284–691 (1984), describes the properties and testing of a representative member of this class of compounds. Preliminary clinical results with these nootropic agents, exemplified by structures 1a)–d), indicate that these drugs may have some beneficial effects in the treatment of senile dementias in the elderly.

Yevich, et al., in U.S. Pat. No. 4,668,687, disclose a series of nootropic compounds of formula 2, wherein

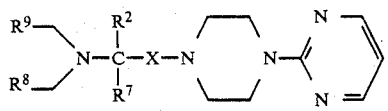

R$^2$ is hydrogen, alkyl, aryl or heterocyclic; R$^7$ is hydrogen or is combined with R$^9$ as a fused benzo-ring; R$^8$ is hydrogen or alkyl; and R$^9$ is alkyl or can be combined with R$^8$ to form a 2-pyrrolidinone, phthalimide, or isoindolone ring system. To our knowledge, the novel tetrahydroisoxazolo[4,5-d]-azepine derivatives comprising the present invention are unrelated structurally to any reported nootropic agent.

The basic heterocycle, 5,6,7,8-tetrahydro-4H-isoxalazolo[4,5-d]azepin-3-ol (also known as THAZ) was described by Krogsgaard-Larsen, et al., in *Acta Chem. Scand.*, B28 (1974) 533–538. In receptor binding studies THAZ has been reported to antagonize both γ-aminobutyric acid (GABA) and glycine binding in certain neurons, cf: P. Krogsgaard-Larsen, et al., *J Neurochem.* 39(5), 1319–1324 (1982); C. Braestrup, et al., ibid 47(3), 691–696 (1986).

The novel THAZ derivatives and their utility of the present invention have not been suggested in any way by prior art.

SUMMARY OF THE INVENTION

Alkyl, allyl and phenalkyl derivatives of 5,6,7,8-tetrahydro-4H-isoxazolo[4,5-d]azepin-3-ol (THAZ) have been found to enhance cerebral functioning such as memory, cognition and learning. These derivatives possess specific antiamnesic properties.

DETAILED DESCRIPTION OF THE INVENTION

The present invention is concerned with alkyl and phenalkyl derivatives of tetrahydro-isoxazolo[4,5-d]azepine having psychocognitive properties and corresponding to structural Formula I. In Formula I, R$^1$ can be

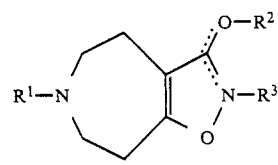

hydrogen, lower alkyl, cycloalkyl, cycloalkyl lower alkyl, allyl, and phenyl-lower alkyl. "Lower" denotes alkyl groups containing from 1 to 6 carbon atoms. R$^2$ and R$^3$ in Formula I are independently selected and can be a non-bonding electron pair, lower alkyl, cycloalkyl, cycloalkyl lower alkyl, allyl and phenyl-lower alkyl. Cycloalkyl denotes carbocyclic rings of 3 to 6 members. It would be evident to one skilled in the art that Formula I represents a structure that comprises an isomeric enol-type relationship (between Ia and Ib) and as such, one of R$^2$ and R$^3$ must always be a non-bonding electron pair. The solid and dotted lines of Formula I represent either a single or a double chemical bond.

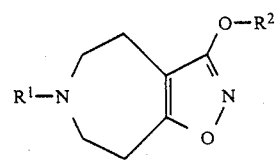

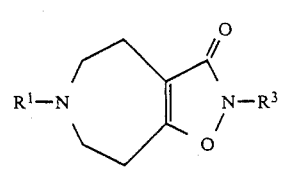

The isomeric structures Ia (enol form) and Ib (keto form) represent 2 classes of compounds: O-substituted and N-substituted isoxazolo moieties, respectively, which comprise the series of compounds of the present invention. Preferred members of these two classes are compounds in which $R^1$ is hydrogen or methyl.

It is to be understood that the present invention is considered to include stereoisomers, e.g. optical isomers including individual enantiomers and mixtures of enantiomers which can arise as a consequence of structural asymetry due to the presence of an asymetric carbon atom which may be incorporated in some compounds of the instant series, such as $R^2/R^3$=2-butyl, etc. Separation of the individual isomers is accomplished by application of various methods which are well known to practitioners in the art.

For medicinal use, the pharmaceutically acceptable acid addition salts, those salts in which the anion does not contribute significantly to toxicity or pharmacological activity of the organic cation, may be preferred in some cases. The acid addition salts are obtained either by reaction of an organic base of structure I with an organic or inorganic acid, preferably by contact in solution, or by any of the standard methods detailed in the literature available to any practitioner skilled in the art. Examples of useful organic acids are carboxylic acids, fumaric acid, isethionic acid, succinic acid, pamoic acid, cyclamic acid, pivalic acid, and the like; useful inorganic acids are hydrohalide acids such as HCl, HBr, HI; sulfuric acids; phosphoric acids; and the like. Additionally, the present invention also encompasses any of the Formula I compounds existing in solvate form such as a hydrate.

The compounds of the instant invention can be conveniently prepared by means of a general process which is shown in Scheme 1.

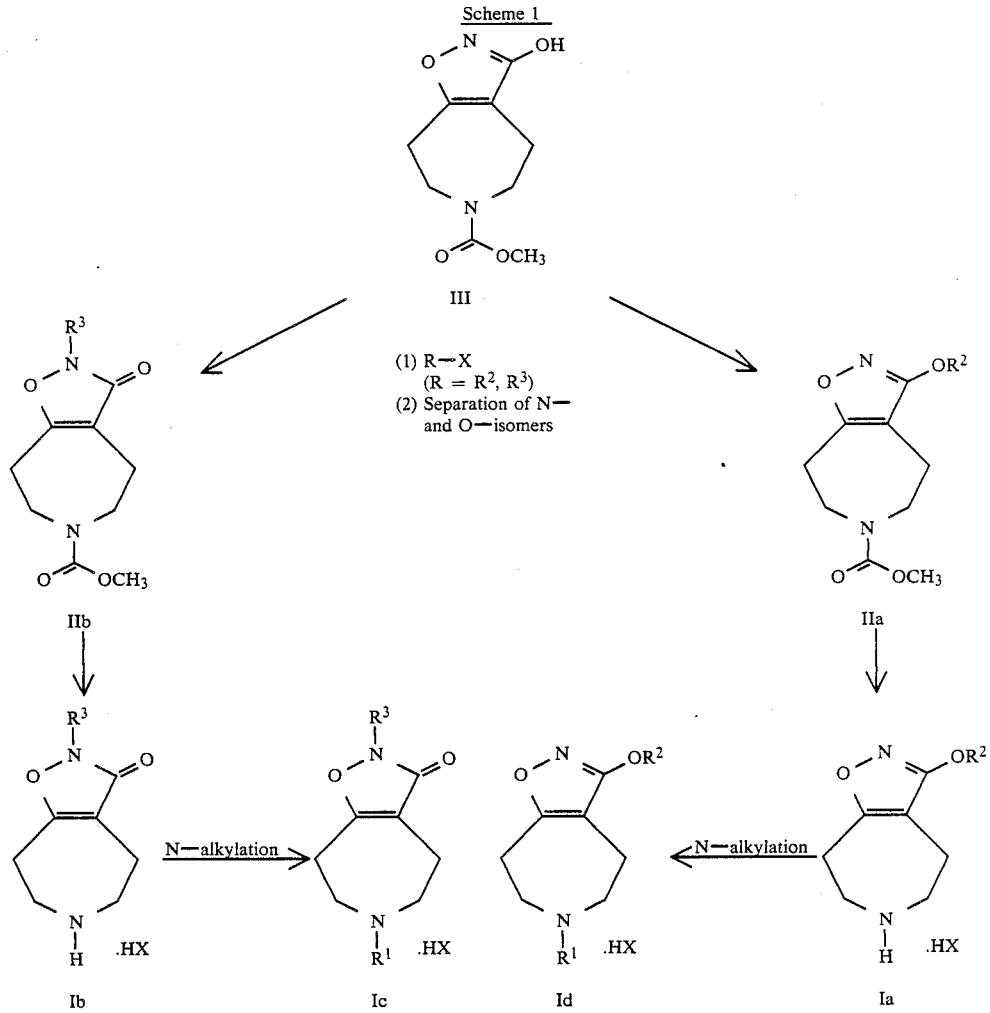

In Scheme 1, methyl 3-hydroxy-5,6,7,8-tetrahydro-4H-isoxazolo[4,5-d]azepine-6-carboxylate (III) is alkylated giving a mixture of N- and O-alkylated products (IIb and IIa, respectively). These alkylated products are separated, e.g. column chromatography, and the individual enol-keto isomers refluxed in alcoholic base thereby cleaving the methyl carboxylate group to provide the 2- and 3-alkylated THAZ derivatives Ia and Ib, respectively.

These mono-alkylated THAZ derivatives, Ia and b, may be further alkylated (using any of a number of standard procedures) at the 6-position to provide dialkylated products Id and Ic.

Using this basic procedural scheme, or selecting from a number of modifications familiar to one skilled in organic synthesis, desired compounds of the present invention may be obtained.

Synthetic intermediate III can be prepared by means of Scheme 2.

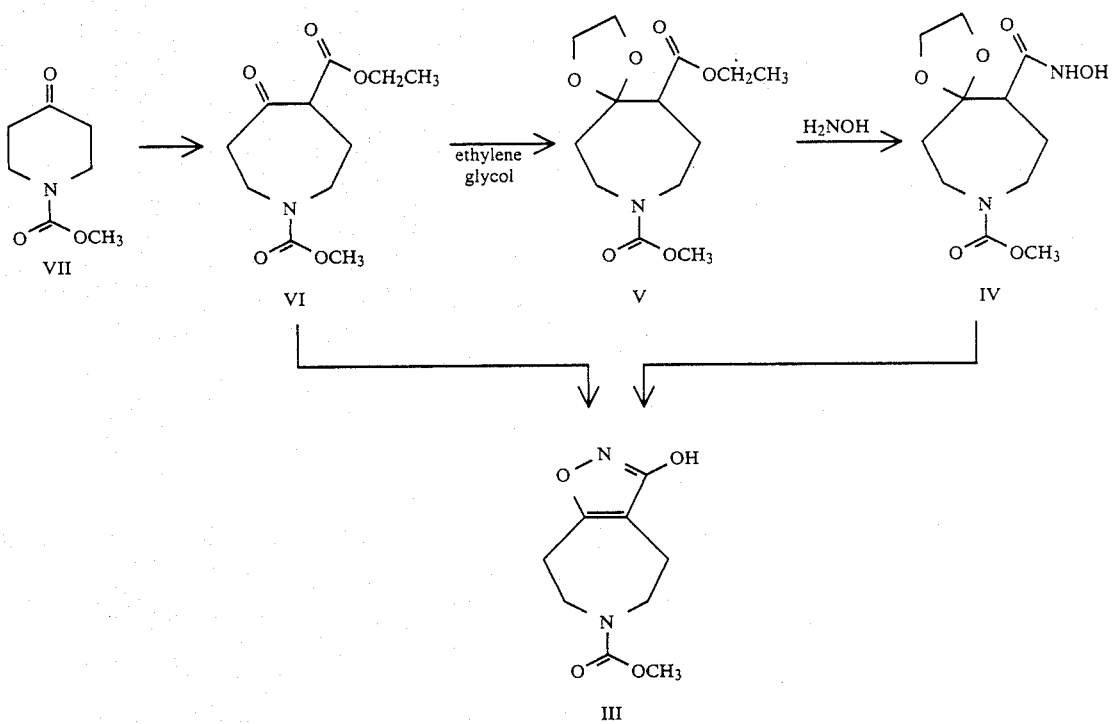

A drawback of the direct conversion process is the formation of the unwanted isomeric product, VIII.

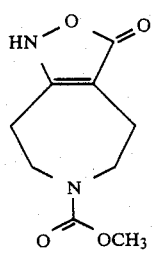

In Scheme 2, the perhydroazepine intermediate VI (prepared from VII according to Krogsgaard-Larsen, et al., *Eur. J. Med. Chem.*, 14 (1979) 157–164) can either be directly converted to III with hydroxylamine or indirectly converted via intermediate compounds V and IV. The ketal intermediate V results from ethylene glycol ketalization of VI, and is in turn converted into the carbohydroxamic acid intermediate IV by reaction with hydroxylamine. De-ketalization and ring-closure of IV in acid medium provides III in the final step of the indirect route.

Compounds of the instant invention have been evaluated for cerebral function enhancing activity using as a primary screen the reversal of electroconvulsive shock-induced amnesia for a step-down passive avoidance response (cf: Banfis, et al., *J. Pharmacol. Meth.*, 8, 225 (1982); Janvik, *Ann. Rev. Psychol.*, 23, 457 (1972); and McGaugh and Petrinovich, *Int. Rev. Neurobiology*, 8, 139 (1965). Reference compounds such as pramiracetam, piracetam, aniracetam, etc., having activity in this paradigm have been purported to affect memory processes and may be useful in treating various dementias due to degenerative processes or diseases such as Alzheimer's disease.

The step-down passive avoidance/ECS-induced amnesia procedure consists of two sessions, a training and test phase. In general, rats not receiving ECS show definite retention of response while animals receiving ECS display amnesia with regard to their inability to remember that descending the platform would result in a footshock. Active test compounds reverse the amnesic effects of the ECS.

Two control groups, sham-ECS (no ECS) control and vehicle-ECS (no drug) control, were employed to evaluate both drug effects and learning levels measured by the step-down passive avoidance task. All drug treated animals received the ECS. The vehicle (deionized water) or the THAZ compounds were orally administered 30 minutes prior to passive avoidance training on day 1. A test compound is considered active at a given dosage level if the mean latency to step-down is both statistically greater than the value for the vehicle-ECS (no drug) control group and not statistically different from the value for the sham-electroconvulsive shock (no ECS) control group. A test compound is considered to have intermediate activity at a given dosage level if results for the drug group are statistically different from both control groups.

Consideration of test results obtained for compounds of the present invention indicate their usefulness in several specific applications wherein such psychocognitive enhancement or normalizing effects on cerebral function would be highly desirable. The subject compounds are intended to be useful in treatment of dementias due to degenerative processes, diseases, and the like; with some specific examples being age-related memory dysfunction; AIDS-related dementia; multiple infarct dementia; Alzheimer's disease; Parkinson-related dementia; and the like. Similarly, the compounds are useful in enhancement of memory and learning processes and for acquisition of new information as well as treating deficits such as those encountered in benign senescent forgetfulness, learning disabilities and certain retardation states, e.g. minimal brain dysfunction. Other uses which are envisioned for the compounds of this invention would be to treat miscellaneous disorders such as dyslexia, aphasia, and Tourette's syndrome.

In addition to the usefulness of the compounds of Formula I as cognition enhancing agents or mild stimulants of neuronal activity, the compounds have been found to be useful in preventing amnesia which results from electroconvulsive shock. Such activity not only relates to memory retention in normal aging and senility processes but would be useful in protecting against the amnesia-producing effects of electroconvulsant shock as it is used clinically. Electroconvulsant shock is employed to treat some classes of psychiatric patients, particularly depressed patients who are refractory to traditional pharmacologic therapy. It is well documented that these electroconvulsant shock treatments induce the undesirable side-effect of amnesia in those patients to whom it is administered. The instant compounds which exhibit activity in protecting against the amnesia-producing effects of electroconvulsant shock in pharmacologic testing would be useful adjuncts to the clinical use of electroconvulsant shock in psychiatric treatment. The compounds are also useful as antiamnesiacs against amnesias induced by drugs, e.g. benzodiazepines, alcohol, etc.; or trauma, e.g. head injury, post-neurosurgery, and so forth.

In summary of the foregoing discussion, the instant compounds have cerebral function enhancing properties particularly suited to their use in treating dementias; cognition and memory enhancement; reversal and/or prevention of amnesia; and certain miscellaneous applications. Thus, another aspect of the instant invention concerns a process for enhancing cerebral function in a mammal in need of such treatment which comprises systemic administration to such mammal of an effective dose of a Formula I compound or a pharmaceutically acceptable acid addition salt thereof. The administration and dosage regimen of a compound of Formula I is considered to be done in the same manner as for the reference compound piracetam, cf: Reisberg, et al., in *Drug Development Research*. 2475-480 (1982); Weng, et al., in *Rational Drug Therapy*. 17(5), 1-4 (1983); Reisberg, et al., in "Psychopathology in the Aged", Editors, Cole and Barrett, Raven Press, New York, pages 243-245 (1980) and pramiracetam, cf: Butler, et al., *J. Med. Chem.*. 27, pp. 684-691 (1984).

Although the dosage and dosage regimen must in each case be carefully adjusted, utilizing sound professional judgment and considering the age, weight and condition of the recipient, the route of administration and the nature and extent of mental deterioration, generally, the daily dose will be from about 0.1 g to about 10 g, preferably 0.5 g to 5 g, when given orally. In some instances, a sufficient therapeutic effect can be obtained at lower doses while in others, larger doses will be required. As is apparent to one skilled in clinical pharmacology, the amount of Formula I compound comprising the daily dose may be given in a single or divided dose, taking into account those principles understood by the skilled practitioner and necessary for his practice of the art.

The term "systemic administration" as used herein refers to oral, sublingual, buccal, nasal, dermal, rectal, intramuscular, intravenous, and subcutaneous routes. Generally, it will be found that when a compound of the present invention is administered orally which is the preferred route, a slightly larger quantity of the active drug may be required to produce the same effect as a somewhat smaller quantity when given parenterally. In accordance with good clinical practice, it is preferred to administer the instant compounds at a concentration level which will produce effective beneficial effects without causing any harmful or untoward side effects.

Therapeutically, the instant compounds are generally given as pharmaceutical compositions comprised of an effective cerebral function enhancing amount of a compound of Formula I or a pharmaceutically acceptable acid addition salt thereof and a pharmaceutically acceptable carrier. Pharmaceutical compositions for effecting such treatment will contain a major or minor amount (e.g. from 95% to 0.5%) of at least one compound of the present invention in combination with a pharmaceutical carrier, the carrier comprising one or more solid, semi-solid, or liquid diluent, filler and formulation adjuvant which is non-toxic, inert and pharmaceutically acceptable. Such pharmaceutical compositions are preferably in dosage unit forms; i.e., physically discrete units having a pre-determined amount of the drug corresponding to a fraction or multiple of the dose which is calculated to produce the desired therapeutic response. In usual practice, the dosage units contain 1, $\frac{1}{2}$, $\frac{1}{4}$ or less of a single dose. A single dose preferably contains an amount sufficient to produce the desired therapeutic effect upon administration at one application of one or more dosage units according to the pre-determined dosage regimen, usually a whole, half, third, or less of the daily dosage administered once, twice, three, or more times a day. It is envisioned that other therapeutic agents can also be present in such a composition. Pharmaceutical compositions which provide from 0.1 to 1 g of the active ingredient per unit dose are preferred and are conventionally prepared as tablets, lozenges, capsules, powder, aqueous or oily suspensions, syrups, elixirs, and aqueous solutions. Preferred oral compositions are in the form of tablets, capsules, and may contain conventional excipients such as binding agents (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from about 0.1% to 10% by weight of the active compound in water or a vehicle consisting of a polyhydric aliphatic alcohol such a glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

DESCRIPTION OF SPECIFIC EMBODIMENTS

The compounds which constitute this invention and their methods of preparation as well as their biological activity will appear more fully from a consideration of the following examples which are given for the purpose of illustration only and are not to be construed as limiting the invention in sphere or scope. All temperatures are understood to be in degrees C when not specified. The nuclear magnetic resonance (NMR) spectral characteristics refer to chemical shifts (δ) expressed in parts per million (ppm) versus tetramethylsilane (TMS) as reference standard except in D$_2$O where sodium 3-(trimethylsilyl)propanesulfonate was used. The relative area reported for the various shifts in the proton ($^1$HMR) spectral data corresponds to the number of hydrogen atoms of a particular functional type in the molecule. The nature of the shift as to multiplicity is reported as broad singlet (bs), singlet (s), multiplet (m), doublet (d), doublet of doublet (dd), triplet (t), or quartet (q). Abbreviations employed are DMSO-d$_6$ (perdeuterodimethylsulfoxide), CDCl$_3$ (deuterochloroform) and are otherwise conventional. The infrared (IR) spectral descriptions include only absorption wave numbers (cm$^{-1}$) having functional group identification value. All compounds gave satisfactory elemental analysis (within ±0.4% of theoretical values). TLC and column chromatography (cc) were accomplished by using silica gel (SiO$_2$) F$_{254}$ plates (Merck) and silica gel (Woelm 0.063-0.100 mm), respectively. Columns were developed by stepwise gradient elution.

EXAMPLE 1

Ethyl 1-methoxycarbonyl-4-oxoperhydroazepine-5-carboxylate ethylene ketal (V)

A mixture of ethyl 1-methoxycarbonyl-4-oxoperhydroazepine-5-carboxylate (VI; cf: Krogsgaard-Larsen, et al., *Eur. J. Med. Chem.*. 14 (1979) pp. 157-164) (26.9 g; 0.11 mol), ehtylene glycol (30.7 mL; 0.55 mol), 4-toluenesulphonic acid hydrate (2.11 g; 11 mmol), and toluene (200 mL) was refluxed in a Dean-Stark water separator for 4 h. Upon addition of toluene (200 mL) the reaction mixture was washed with a saturated solution of sodium bicarbonate (50 mL), dried (K$_2$CO$_3$) and evaporated to give crude (V), which was used without further purification as starting material for the synthesis of (IV).

EXAMPLE 2

1-Methoxycarbonyl-4-oxoperhydroazepine-5-carbohydroxamic acid ethylene ketal (IV)

To a solution of hydroxylamine hydrochloride (11.6 g; 0.17 mol) in methanol (80 mL) was added at 40° C. and with stirring a solution of sodium methoxide in methanol (80 mL) prepared from 7.7 g (0.33 mol) of sodium. To this solution was added at 0° C. a solution of crude (V) (31.6 g; ca. 0.11 mol) in methanol (40 mL). This mixture was left at 25° C. with stirring for 24 h, and after cooling to 0° C. and with continued stirring, pH of the solution was adjusted to ca. 3 by addition of a solution of hydrogen chloride in ethyl acetate (2.5 M). The filtered and evaporated reaction mixture was extracted with ethyl acetate, and after filtration and addition of light petroleum (50 mL) compound (IV) crystallized. The yield of (IV) was 12.0 g (39%), M.p. 152.0–154.0° C. Anal. C$_{11}$H$_{18}$N$_2$O$_6$.

EXAMPLE 3

Methyl 3-hydroxy-5,6,7,8-tetrahydro-4H-isoxazolo[4,5-d]-azepine-6-carboxylate (III

Method A

To a solution of (IV) (12.0 g; 0.044 mol) in methanol (45 mL) was added at 80° C. concentrated hydrochloric acid (45 mL). After continued heating at 80° C. for 15 min, the reaction mixture was evaporated to ca. 40 mL and then extracted with chloroform (3×100 mL). The combined organic phases were dried (MgSO$_4$), filtered and evaporated. The residue was recrystallized from ethyl acetate to give (III) (5.45 g; 58%), M.p. 127.0°–128.0° C. Anal. C$_9$H$_{12}$N$_2$O$_4$.

Method B

To a solution of hydroxylamine hydrochloride (2.86 g; 0.041 mol) in an aqueous solution of sodium hydroxide (20 mL; 2 M) (pH 10.0) was added dropwise and with stirring at 0° C. compound (VI) (10.0 g; 0.041 mol). By simultaneous dropwise addition of an aqueous solution of sodium hydroxide (2 M), p was kept at 10±0.2. After termination of the addition of (VI), stirring of the reaction mixture was continued at 0° C. for 1 h, and during this period pH of the solution was kept at 10±0.2 as described above. The reaction mixture (0° C.) was added to concentrated hydrochloric acid (30 mL) at 0° C., and this mixture was extracted with dichloromethane (3×150 mL). The combined organic phases were dried (MgSO$_4$) and evaporated and the residue subjected to CC [SiO$_2$: 150 g; eluent: toluene-ethyl acetate (1:1) containing glacial acetic acid (2%)]. The fractions containing the unwanted side-product, 1,3,4,5,7,8-hexahydro-3-oxo-6H-isoxazolo[3,4-d]azepine-6-carboxylate (VIII) were discarded. The yield of (III) was 3.68 g (42%). The IR spectrum of this sample of (5) was identical with that of (III) prepared by Method A.

Method C

To an aqueous solution (30 mL; pH 9.86) of hydroxylamine hydrochloride (0.56 g; 0.008 mol) and sodium carbonate (3.39 g; 0.032 mol) was added dropwise and with stirring at 25° C. a solution of (VI) (1.95 g; 0.008 mol) in methanol (4 mL). After termination of the addition of (VI), pH of the solution was 9.63, and stirring was continued at 25° C. for 45 min. The reaction mixture was added to concentrated hydrochloric acid (8 mL) at 25° C., and this mixture was extracted with chloroform (3×50 mL). The combined organic phases were dried (MgSO$_4$) and evaporated and the residue subjected to CC [SiO$_2$:60 g; eluent: tolueneethyl acetate (1:1) containing glacial acetic acid (2%)]. The fractions containing (VIII) were discarded. The yield of (5) was 214 mg (13%). The IR spectrum of this sample of (III) was identical with that of (III) prepared by Method A.

EXAMPLE 4

Syntheses of methyl 3-alkoxy-5,6,7,8-tetrahydro-4H-isoxazolo-[4,5-d]azepine-6-carboxylate (IIa) and methyl 2-alkyl-1,3,4,5,7,8-hexahydro-3-oxo-6H-isoxazolo[4,5-d]azepine-6-carboxylates (IIb)

General Procedure

To a solution of (III) (6.37 g; 0.030 mol) in acetone (90 mL) was added potassium carbonate (10.4 g; 0.075 mol), and the mixture was refluxed for 30 min. To this mixture was added the appropriate alkyl, allyl or phenylalkyl halide. The reaction mixture was refluxed for 24 h, filtered, and evaporated. The residue was subjected to CC [$SiO_2$: 200 g; eluents: toluene-ethyl acetate (2:1) and, subsequently, ethyl acetate neat]in order to separate the N-and O-alkylated products, IIb and IIa. To avoid unwanted rearrangement/elimination reactions which can occur in cycloalkyl alkylation reactions, reductive alkylation of III with a cycloalkanone and sodium cyanoborohydride may be employed.

EXAMPLE 5

Methyl 3-methoxy-5,6,7,8-4H-isoxazolo[4,5-d]azepine-6-carboxylate (IIa) and methyl 2-methyl-1,3,4,5,7,8-hexahydro-3-oxo-6H-isoxazolo[4,5-d]azepine-6-carboxylate (IIb)

(IIa):

Using the procedure of Example 4 and methyl iodide as the alkyl halide, the two isomeric II products were obtained. Yield 37% M.p. 94.0°–96.0° C. Anal. $C_{10}H_{14}N_2O_4$.

IR (KBr) $cm^{-1}$: 2970–2580 (m-w, several bands); 1695 (s), 1655 (s), 1480 (m).

$^1$H NMR (CDCl$_3$) δ: 4.05 (3H, s), 3.79 (3H, s), 3.8–3.5 (4H, broad t), 3.1–2.8 (2H, broad t), 2.7–2.4 (2H, broad t).

(IIb):

Yield: 30% M.p. 116.0°–118.0° C. Anal. $C_{10}H_{14}N_2O_4$.

IR (KBr) $cm^{-1}$: 3000–2750 (m-w, several bands); 1685 (s), 1635 (m), 1520 (s).

$^1$H NMR (CDCl$_3$) δ: 3.77 (3H, s), 3.48 (3H, s), 3.8–3.4 (4H, broad t), 2.9–2.3 (4H, m).

Using the procedure of Example 4 and the appropriate alkyl halide (e.g. ethyl iodide, propyl bromide, benzyl bromide, etc.); other IIa and IIb intermediates are prepared.

EXAMPLE 6

3-Methoxy-5,6,7,8-tetrahydro-4H-isoxazolo[4,5-d]azepinium chloride (O-Methyl-THAZ,HCl) (Ia; $R^2$=Me)

A solution of (IIa; R=Me) (4.53 g; 0.02 mol) in a methanolic solution of potassium hydroxide (40 mL; 4 M) was refluxed for 48 h. The evaporated reaction mixture was extracted with chloroform (3×75 mL). The combined organic phases were dried (MgSO$_4$) and evaporated. The residue was dissolved in a methanolic solution of hydrogen chloride (20 mL; 3 M), and upon addition of ethyl acetate (30 mL) crude (7 c) crystallized. After recrystallization (methanol-ethyl acetate-light petroleum) 3.05 g (74%) of the desired Ia product was obtained. M.p. 201.0°–202.0° C. Anal. $C_8H_{13}ClN_2O_2$.

IR (KBr) $cm^{-1}$: 3100–2300 (s-m, several bands), 1660 (m), 1560 (s), 1550 (s), 1530 (s).

$^1$H NMR (D$_2$O) δ: 4.00 (3H, s), 3.7–3.4 (4H, m), 3.4–3.1 (2H, broad t), 2.9–2.7 (2H, broad t).

EXAMPLE 7

2-Methyl-1,3,4,5,7,8-hexahydro-3-oxo-6H-isoxazolo[4,5-d]azepinium bromide (2-Methyl-THAZ,HBr) (Ib; $R^3$=Me)

A solution of (IIb; R=Me) (3.50 g; 0.016 mol) in a solution of hydrogen bromide in glacial acetic acid (35 mL; 33%) was left at 25° C. for 48 h and then evaporated. The residue was recrystallized (methanol-ether) to give 3.19 g (83%) of the desired Ib product. M.p. 171.0°–173.0° C. Anal. $C_8H_{13}BrN_2O_2$.

IR (KBr) $cm^{-1}$:3340 (s), 3210 (m), 3000–2420 (s-m, several bands), 1650 (s), 1630 (s), 1485 (m).

$^1$H NMR (D$_2$O) δ: 3.65 (3H, s), 3.7–3.4 (4H, m), 3.3–3.1 (2H, m), 2.9–2.7 (2H, broad t).

EXAMPLE 8

2-Ethyl-1,3,4,5,7,8-hexahydro-3-oxo-6H-isoxazolo[4,5-d]azepinium hydrogenfumarate (2-Ethyl-THAZ,hydrogenfumarate) (Ib; $R^3$=Et)

A solution of (IIb; R=Et) (5.15 g; 0.024 mol) in a solution of hydrogen bromide in glacial acetic acid (30 mL; 33%) was left at 25° C. for 72 h and then evaporated. The residue was dissolved in water (30 mL), and upon addition of sodium carbonate (6 g) the mixture was extracted with chloroform (3×50 mL). The combined organic phases were dried (MgSO$_4$) and evaporated to give 2.86 g (ca. 0.016 mol) of crude oily 2-ethyl-THAZ. This residue was dissolved in a mixture of ethanol (2 mL) and ether (20 mL), and a solution of fumaric acid (1.86 g; 0.016 mol) in 2-propanol (25 mL) was added. The precipitate of crude Ib product was recrystallized (methanol-ether) to give 4.12 g (65%) of the title compound, M.p. 174.0°–176.0° C. Anal. $C_{13}H_{18}N_2O_6$.

IR (KBr) $cm^{-1}$: 3600–3200 (m, broad signal), 3010–2400 (s-m, several bands), 1690 (s), 1665 (s), 1480 (w).

$^1$H NMR (D$_2$O) δ: 6.63 (2H, s), 3.96 (2H, q, j 7 Hz), 3.5–3.3 (4H, m), 3.2–3.0 (2H, broad t), 2.7–2.5 (2H, broad t), 1.24 (3H, t, J 7 Hz).

EXAMPLE 9

2-Propyl-1,3,4,5,7,8-hexahydro-3-oxo-6H-isoxazolol[4,5-d]azepinium hydrogenfumarate (2-Propyl-THAZ,hydrogenfumarate) (Ib; $R^3$=Pr)

A solution of (IIb; R=Pr) (1.01 g; 0.004 mol) in a solution of hydrogen bromide in glacial acetic acid (8 mL; 33%) was left at 25° C. for 72 h and then evaporated. The residue was mixed with an aqueous solution of sodium hydroxide (30 mL; 1 M), and this mixture was extracted with dichloromethane (3×25 mL). The combined organic phases were washed with a saturated aqueous solution of sodium hydrogencarbonate (25 mL), dried (MgSO$_4$), and evaporated to give 0.83 g (ca. 0.004 mol) of crude oily 2-propyl-THAZ. This residue was dissolved in 2-propanol (4 mL) and a solution of fumaric acid (0.46 g; 0.004 mol) in 2-propanol (4 mL) was added. The precipitate of crude Ib product was recrystallized (methanol-ether) to give 0.87 g (70%) pure Ib product, M.p. 189° C. (decomp.). Anal. $C_{14}H_{20}N_2O_6$.

IR (KBr) cm$^{-1}$: 3600–3300 (m, broad signal), 3010 (m), 2865–2400 (m-w, several bands), 1690 (s), 1665 (s).

$^1$H NMR (D$_2$O) δ: 6.61 (2H, s), 3.87 (2H, t, J 6 Hz), 3.5–3.3 (4H, m), 3.07 (2H, t, 5 Hz), 2.65 (2H, t, J 5 Hz), 1.8–1.5 (2H, m), 0.80 (3H, t, J 7 Hz).

EXAMPLE 10

2-Benzyl-1,3,4,5,7,8-hexahydro-3-oxo-6H-isoxazolo[4,5-d]azepinium hydrogenfumarate (2-Benzyl-THAZ, hydrogenfumarate) (Ib; R$^3$=CH$_2$Ph)

Compound (IIb; R=CH$_2$Ph) (3.75 g; 0.012 mol) was deprotected following a procedure analogous with that described above in Example 9. To a solution of crude 2-benzyl-THAZ (2.39 g; 0.01 mol) in 2-propanol (5 mL) was added a solution of fumaric acid (1.16 g; 0.01 mol) in 2-propanol (10 mL). The precipitate was recrystallized (methanol-ether) to give 3.14 g (70%) of desired product, M.p. 152° C. (decomp.). Anal. C$_{18}$H$_{20}$N$_2$O$_6$.

IR (KBr) cm$^{-1}$: 3600–3300 (m, broad band), 3030 (w), 2980–2350 (m-w, several bands), 1705 (s), 5.06 (2H, s), 3.5–3.3 (4H, m), 3.1–2.9 (2H, broad t), 2.7–2.5 (2H, broad t).

EXAMPLE 11

2,6-Dimethyl-1,3,4,5,7,8-hexahydro-3-oxo-6H-isoxazolo[4,5-d]azepinium chloride (2,6-Dimethyl-THAZ,HCl) (Ic; R$^1$=R$^3$=Me)

A solution of (Ib; R$^3$=Me) (2.50 g; 0.01 mol) in water (30 mL), adjusted to pH ca. 12 by addition of potassium carbonate, was extracted with dichloromethane (3×50 mL). The combined organic phases were evaporated and the oily residue dissolved in a mixture of aqueous solutions of formic acid (25 mL; 98%) and formaldehyde (25 mL; 40%). This solution was refluxed for 4 h and then evaporated. A mixture of the oily residue and water (8 mL), adjusted to pH ca. 12 by addition of potassium carbonate, was extracted with chloroform (3×100 mL). The combined, dried (MgSO$_4$), and evaporated organic phases were dissolved in ethyl acetate (5 mL), and upon addition of a solution of hydrogen chloride in ethyl acetate (10 mL); 1 M) crude product precipitated. Recrystallization (ethanol-ether) afforded 1.45 g (66%) of the title compound, M.p. 215° C. (decomp.) Anal. C$_9$H$_{15}$ClN$_2$O$_2$.

IR (KBr) cm$^{-1}$: 3000–2780 (m-w, several bands), 2760–2100 (s, several bands), 1665 (s), 1470 (m), 1460 (m), 1440 (m), 1415 (m).

$^1$H NMR (D$_2$O) δ3.6–3.4 (4H, m), 3.52 (3H, s), 3.2–3.0 (2H, broad t), 2.97 (3H, s), 2.8–2.6 (2H, broad t).

EXAMPLE 12

2-Ethyl-6-methyl TM 1,3,4,5,7,8-hexahydro-3-oxo-6H-isoxazolo4,5-d]azepinium hydrogenfumarate (2-Ethyl-6-Methyl-THAZ,hydrogenfumarate) (Ic; R$^1$=Me, R$^3$=Et)

The N-methylation of (Ib; R$^3$=Et) (0.89 g; 0.003 mol) was accomplished following a procedure analogous with that described above in Example 11. To a solution of crude 2-ethyl-6-methyl-THAZ (0.54 g; ca. 0.0028 mol) in 2-propanol (2 mL) was added a solution of fumaric acid (0.32 g: 0.0028 mol) in 2-propanol (5 mL). Upon addition of ether (5 mL) crude fumarate salt slowly precipitated. Recrystallization (methanol-ether) afforded 0.99 g (66%) of product, M.p. 126.0°–128.0° C. Anal. C$_{14}$H$_{20}$N$_2$O$_6$.

IR (KBr) cm$^{-1}$: 3000–2750 (m-w, several bands), 2730–2200 (s-m, several bands), 1660 (s), 1465 (m), 1460 (m), 1450 (m).

$^1$H NMR (D$_2$O) δ:6.61 (2H, s), 3.95 (2H, q, J 7 Hz), 3.6–3.4 (4H, m), 3.2–3.0 (2H, broad t), 2.99 (3H, s), 2.8–2.6 (2H, broad t), 1.27 (3H, t, J 7 Hz).

EXAMPLE 13

2-Propyl-6-methyl-1,3,4,5,7,8-hexahydro-3-oxo-6H-isoxazolo[4,5-d]azepinium sesquihydrogenfumarate (2-Propyl-6-Methyl-THAZ,sesquihydrogenfumarate) (Ic; R$^1$=Me; R$^3$=Pr)

The N-methylation of (Ib, R$^3$=Pr) (0.42 g; 0.0015 mol) was accomplished following a procedure analogous with that described in Example 11. To a solution of crude 2-propyl-6-methyl-THAZ (0.29 g; ca. 0.0015 mol) in 2-propanol (2 mL) was added a solution of furmaric acid (0.27 g; 0.0023 mol) in 2-propanol (4 mL) Upon addition of eth (8 mL) crud fumarate salt slowly precipitated. Recrystallization (methanol-ether) afforded 0.26 g (45%) of product, M.p. 124.0°–126.0° C. Anal. C$_{17}$H$_{24}$N$_2$O$_8$.

IR (KBr) cm$^{-1}$: 2980–2770 (m-w, several bands), 2740–2200 (s-m, several bands), 1710 (s), 1660 (s), 1625 (s), 1455 (m).

$^1$H NMR (D$_2$O) δ: 6.72 (3H, s), 3.92 (2H, t, J 6 Hz), 3.7–3.5 (4H, m), 3.2–3.0 (2H, broad t), 3.01 (3H, s), 2.8–2.6 (2H, broad t), 1.9–1.6 (2H, m), 0.84 (3H, t, J 6.5 Hz).

EXAMPLE 14

2,6-Dialkyl-1,3,4,5,7,8-hexahydro-3-oxo-6H-isoxazolo[4,5-d]azepine, 1c (2,6-Dialkyl THAZ)

In a typical preparation, a compound of type 1b, along with an equimolar quantity or slight excess of anhydrous potassium carbonate in an aprotic solvent, such as acetonitrile or tetrahydrofuran is treated by addition of an equimolar quantity of an appropriate alkyl halide in a minimal amount of the same solvent. The resultant mixture is heated under reflux for a period of 1–24 h, filtered and the filtrate concentrated in vacuo. The residual material is either recrystallized from an appropriate solvent to afford 2,6-dialkyl THAZ free base or treated with ethanolic HCl or with an organic acid such as fumaric or maleic acid to afford the corresponding salt. The 6-alkyl group introduced by this general procedure may be lower alkyl, phenyl-lower alkyl, cycloalkyl-lower alkyl and allyl.

EXAMPLE 15

6-Alkyl-2-alkoxy-4,5,7,8-tetrahydro-6H-isoxazolo[4,5-d]azepine, 1d (6-Alkyl-2-alkoxy-THAZ)

Compound of this type may be obtained via the above procedure employing a compound of type 1a as the starting material.

EXAMPLE 16

2-Alkyl-6-cycloalkyl-1,3,4,5,6,7-hexahydro-3-oxo-6H-isoxazolo[4,5-d]azepine, 1c (2-Alkyl-6-cycloalkyl THAZ)

A typical preparation is performed according to the procedure of Borch, et al., *J. Amer. Chem. Soc.*, 93, 2897 (1971). A solution of equimolar quantities of a compound of type 1b and a cycloalkanone and a slight excess of one-third equivalent of sodium cyanoborohydride in methanol or ethanol is stirred at room temperature for 1-3 h, diluted with aqueous NaCl solution and extracted with ether or chloroform. The organic extract is washed with several portions of water, dried over anhydrous sodium or magnesium sulfate, filtered and concentrated in vacuo. The residual material is either recrystallized from an appropriate organic solvent to give 2-alkyl-6-cycloalkyl THAZ free base or treated with ethanolic HCl or with an organic acid such as fumaric or maleic acid to provide the corresponding salt.

EXAMPLE 17

2-Alkoxy-6-cycloalkyl-4,5,7,8-tetrahydro-6H-isoxazolo[4,5-d]azepine, 1d (2-Alkoxy-6-cycloalkyl THAZ)

Compounds of this type may be obtained via the above procedure employing a compound of type 1a as the starting material.

EXAMPLE 18

Reversal of ECS-induced Amnesia for Step-Down Passive Avoidance Response

In the step-down passive avoidance procedure, rats are trained to remain immobile to avoid foot shock. Two control groups are required: a vehicle-only-ECS group and a vehicle-only-no-ECS group.

Training Session—Day 1

Animals were first individually fitted with auricular electrodes and placed upon the safe zone platform. Animals descending the platform in less than 60 seconds, immediately experienced a 1.0 mA footshock for 2 seconds. Animals were then given a 3 second rest period whereupon they received ECS and were promptly removed from the chamber and placed in their home cages. Rats attempting to ascend the platform during the foot shock or rest period immediately received ECS and were removed from the test chamber. The sham-ECS controls were identically handled; however, they did not receive ECS. Animals not descending from the platform within 60 seconds were returned to their home cages and not used in the study. Rats stepping down in less than 5 seconds were also omitted from further testing. pcl Test Session and Evaluation of Performance—Day 2

After 21 hours, animals were retested for retention of the passive avoidance response. Animals were individually placed upon the platform and their step-down latencies recorded. Animals remaining atop the platform for 120 seconds were considered to be amnesic.

The quantal results are calculated in both fractions and percentages and significance determined by statistical evaluation. Fractions were obtained by using the following ratio:

$$\frac{\text{Number of animals retaining}}{\text{Number of animals tested}}$$

Percentages are expressed as the percentage of sham-ECS control performance which was assigned an arbitrary value of 100 using the following formula:

$$\frac{\% \text{ of observed retaining animals}}{\% \text{ of observed retaining sham-ECS control}} \times 100$$

Statistical comparisons were made using the 2×2 chi square formula corrected for one degree of freedom.

A compound was considered to be active in this test if the mean retention score obtained from at least one dose group is both significantly greater than the ECS control group retention and not significantly different from the sham-ECS control group, but did not raise the performance sufficiently to be not statistically different from the sham-ECS control group were scored as possessing "intermediate activity". These compounds, then, do statistically raise the animals' performance, but not sufficiently to give total protection against amnesia.

The biological activities of selected Formula I compounds in the test outlined in Example 18 are given in Table 3.

TABLE 3

Biological Activities of Selected Formula I Compounds in Reversal of ECS-induced Amnesia for a Step-Down Passive Avoidance Response

| Example No. and Name | ECS-Induced Amnesia Reversal |
|---|---|
| - pramiracetam (reference compound) | active[a] at 10 mg/kg s.c. |
| 6 3-Methoxy-5,6,7,8-tetrahydro-4H—isoxazolo[4,5-d]azepinium chloride | active at 1 mg/kg p.o. |
| 7 2-Methyl-1,3,4,5,7,8-hexahydro-3-oxo-6H—isoxazolo[4,5-d]-azepinium bromide | active at 10 mg/kg p.o. |
| 8 2-Ethyl-1,3,4,5,7,8-hexahydro-3-oxo-6H—isoxazolo[4,5-d]azepinium hydrogenfumarate | intermediate activity at 0.3 mg/kg p.o. |
| 9 2-Propyl-1,3,4,5,7,8-hexahydro-3-oxo-6H—isoxazolo[4,5-d]azepinium hydrogenfumarate | active at 1 mg/kg p.o. |
| 10 2-Benzyl-1,3,4,5,7,8-hexahydro-3-oxo-6H—isoxazolo[4,5-d]azepinium hydrogenfumarate | active at 1 mg/kg p.o. |
| 11 2,6-Dimethyl-1,3,4,5,7,8-hexahydro-3-oxo-6H—isoxazolo[4,5-d]-azepinium chloride | intermediate activity at 1.0 mg/kg p.o. |
| 12 2-Ethyl-6-methyl-1,3,4,5,7,8-hexahydro-3-oxo-6H—isoxazolo[4,5-d]azepinium hydrogenfumarate | active at 0.1 mg/kg p.o. |
| 13 2-Propyl-6-methyl-1,3,4,5,7,8-hexahydro-3-oxo-6H—isoxazolo[4,5-d]azepinium sesquihydrogenfumarate | minimally active at 10 mg/kg p.o. |
| 19 3-Ethoxy-5,6,7,8-tetrahydro-4H—isoxazolo[4,5-d]azepinium | intermediate activity at 0.1 mg/kg p.o. chloride |

[a]"Active" denotes compounds which completely reversed the ECS-induced amnesia; while "intermediate activity" denotes less than complete protection as described in Example 17.

What is claimed is:
1. A compound of Formula I

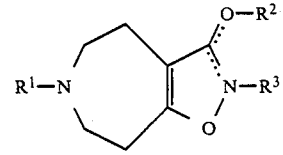

and its pharmaceutically acceptable salts and solvates wherein $R^1$ is hydrogen, lower($C_{1-6}$)alkyl, $C_{3-6}$ cycloalkyl, cycloalkyl-lower alkyl, allyl and phenyl-lower alkyl;

$R^2$ and $R^3$ are independently selected from a non-bonding electron pair, lower alkyl, $C_{3-6}$ cycloalkyl, cycloalkyl-lower alkyl, allyl and phenyl-lower alkyl, with the proviso that one of $R^2$ and $R^3$ is always a non-bonding electron pair; and the solid and dotted line is either a single or double chemical bond.

2. A compound of claim 1 wherein $R^2$ is a non-bonding electron pair.

3. A compound of claim 1 wherein $R^3$ is a non-bonding electron pair.

4. A compound of claim 1 wherein $R^1$ is hydrogen or methyl.

5. The compound of claim 1, 3-Methoxy-5,6,7,8-tetrahydro-4H-isoxazolo[4,5-d]azepine.

6. The compound of claim 1, 2-Methyl-1,3,4,5,7,8-hexahydro-3-oxo-6H-isoxazolo [4,5-d]azepine.

7. The compound of claim 1, 2-Ethyl-1,3,4,5,7,8-hexahydro-3-oxo-6H-isoxazolo[4,5-d]azepine.

8. The compound of claim 1, 2-Propyl-1,3,4,5,7,8-hexahydro-3-oxo-6H-isoxazolo[4,5-d]azepinium hydrogenfumarate.

9. The compound of claim 1, 2-Benzyl-1,3,4,5,7,8-hexahydro-3-oxo-6H-isoxazolo[4,5-d]azepine.

10. The compound of claim 1, 2,6-Dimethyl-1,3,4,5,7,8-hexahydro-3-oxo-6H-isoxazolo[4,5d]azepine.

11. The compound of claim 1, 2-Ethyl-6-methyl-1,3,4,5,7,8-hexahydro-3-oxo-6H-isoxazolo[4,5-d]azepine.

12. The compound of claim 1, 2-Propyl-6-methyl-1,3,4,5,7,8-hexahydro-3-oxo-6H-isoxazolo[4,5-d]azepine.

13. The compound of claim 1, 3-Ethoxy-5,6,7,8-tetrahydro-4H-isoxazolo[4,5-d]azepine.

14. A pharmaceutical composition for enhancing cerebral function in a mammal comprising an effective non-toxic amount of a compound of claim 1 and a pharmaceutically acceptable carrier.

15. A method for enhancing cerebral function in a mammal in need of such treatment comprising administering an amount of a compound of claim 1 effective in enhancing cerebral function.

* * * * *

UNITED STATES PATENT AND TRADEMARK OFFICE
CERTIFICATE OF CORRECTION

PATENT NO. : 4,859,666

DATED : August 22, 1989

INVENTOR(S) : Michael S. Eison, et al

It is certified that error appears in the above-identified patent and that said Letters Patent is hereby corrected as shown below:

In claim 8, lines 2 and 3, replace "azepinium hydrogenfumarate" with --azepine--.

Signed and Sealed this

Thirty-first Day of July, 1990

Attest:

HARRY F. MANBECK, JR.

Attesting Officer      Commissioner of Patents and Trademarks